United States Patent
Sathe et al.

(10) Patent No.: US 11,034,683 B2
(45) Date of Patent: Jun. 15, 2021

(54) PROCESS FOR THE PREPARATION OF RIVAROXABAN INVOLVING NOVEL INTERMEDIATE

(71) Applicant: Unichem Laboratories Ltd, Maharashtra (IN)

(72) Inventors: Dhananjay G. Sathe, Maharashtra (IN); Arijit Das, Goa (IN); Sanjay Raikar, Goa (IN); Yashwant S. Surve, Maharashtra (IN); Bhushan S. Pandit, Maharashtra (IN)

(73) Assignee: UNICHEM LABORATORIES LTD, Maharashtra (IN)

( * ) Notice: Subject to any disclaimer, the term of this patent is extended or adjusted under 35 U.S.C. 154(b) by 0 days.

(21) Appl. No.: 16/335,506

(22) PCT Filed: Dec. 21, 2017

(86) PCT No.: PCT/IB2017/058245
§ 371 (c)(1),
(2) Date: Mar. 21, 2019

(87) PCT Pub. No.: WO2018/127762
PCT Pub. Date: Jul. 12, 2018

(65) Prior Publication Data
US 2020/0017487 A1    Jan. 16, 2020

(30) Foreign Application Priority Data

Jan. 4, 2017   (IN) .............................. 201721000351

(51) Int. Cl.
*C07D 413/14* (2006.01)
*C07D 413/10* (2006.01)

(52) U.S. Cl.
CPC ......... *C07D 413/14* (2013.01); *C07D 413/10* (2013.01); *C07B 2200/13* (2013.01)

(58) Field of Classification Search
CPC ........................... C07D 413/14; C07D 413/10
USPC ........................ 548/229; 544/137, 146, 170
See application file for complete search history.

(56) References Cited

U.S. PATENT DOCUMENTS

| | | |
|---|---|---|
| 2007/0004712 A1 | 1/2007 | Selvakumar et al. |
| 2015/0126733 A1 | 5/2015 | Dodda et al. |
| 2015/0166568 A1 | 6/2015 | Straub et al. |

FOREIGN PATENT DOCUMENTS

| | | | |
|---|---|---|---|
| WO | WO-2013053739 A1 * | 4/2013 | ........... C07D 413/14 |
| WO | 2015/198259 | 12/2015 | |

OTHER PUBLICATIONS

Trummal, A., L. Lipping, I. Kaljurand, I. Koppel and I. Leito, "Acidity of strong acids in water and dimethyl sulfoxide", J. Phys. Chem. A 2016, 120, 20, pp. 3663-3669. (Year: 2016).*
International Search Report issued in PCT/IB2017/058245 dated May 2, 2018 (3 pages).

* cited by examiner

*Primary Examiner* — Joseph R Kosack
*Assistant Examiner* — Sagar Patel
(74) *Attorney, Agent, or Firm* — Cozen O'Connor

(57) ABSTRACT

The present invention relates to the novel key intermediate, 4-{4-[(5S)-(Aminomethyl)-2-oxo-1,3-oxazolidin-3-yl]-phenyl}-morpholin-3-one perchlorate, in the synthesis of rivaroxaban. The invention further relates to the crystalline form of novel intermediate, the process to prepare the novel intermediate and method of preparing rivaroxaban using this novel intermediate. The invention provides an improved and efficient process for preparation of Rivaroxaban.

14 Claims, 3 Drawing Sheets

Fig 1A: XRPD pattern of Compound of Formula-5
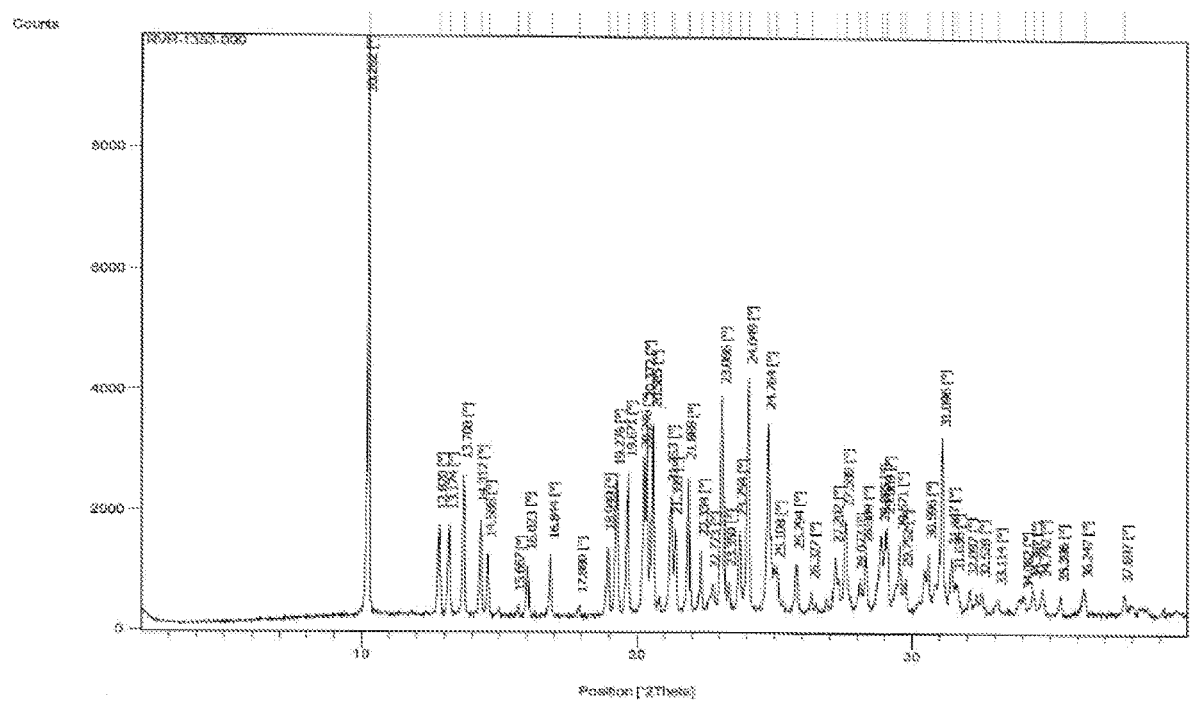

Fig 1B: List of Peaks as depicted in XRPD pattern in Fig 1A

Peak List

| Pos.(°2Th.) | Height(cts) | FWHM(°2Th.) | d-spacing(Å) | Rel.Int.(%) |
|---|---|---|---|---|
| 10.2615 | 9785.88 | 0.0802 | 8.61351 | 100.00 |
| 12.8138 | 1543.43 | 0.0802 | 6.89980 | 15.80 |
| 13.1736 | 1540.35 | 0.0803 | 6.71528 | 15.72 |
| 13.7080 | 2369.30 | 0.0803 | 6.45467 | 24.26 |
| 14.3169 | 1660.46 | 0.0803 | 6.18151 | 16.90 |
| 14.5883 | 1062.28 | 0.0802 | 6.06709 | 10.86 |
| 15.6672 | 171.04 | 0.1203 | 5.65163 | 1.75 |
| 16.0226 | 873.87 | 0.1003 | 5.52706 | 8.93 |
| 16.8436 | 1049.82 | 0.0802 | 5.25948 | 10.74 |
| 17.8797 | 148.05 | 0.1203 | 4.95695 | 1.52 |
| 18.9488 | 1164.13 | 0.0802 | 4.67961 | 11.90 |
| 19.2758 | 2251.80 | 0.0803 | 4.60097 | 23.02 |
| 19.6712 | 2378.66 | 0.0803 | 4.50936 | 24.35 |
| 20.2456 | 2498.96 | 0.0802 | 4.38272 | 25.59 |
| 20.3720 | 3345.11 | 0.0803 | 4.35581 | 34.25 |
| 20.5852 | 3193.60 | 0.0602 | 4.31117 | 32.70 |
| 21.2525 | 1925.99 | 0.0802 | 4.17728 | 19.72 |
| 21.3991 | 1389.38 | 0.0802 | 4.14906 | 14.23 |
| 21.8876 | 2283.73 | 0.0803 | 4.05748 | 23.38 |
| 22.3340 | 1019.86 | 0.1003 | 3.97740 | 10.44 |
| 22.7738 | 476.10 | 0.0802 | 3.90173 | 4.88 |
| 23.0860 | 3534.12 | 0.1004 | 3.84951 | 36.12 |
| 23.3497 | 506.84 | 0.0803 | 3.80663 | 5.19 |
| 23.7542 | 1341.12 | 0.1003 | 3.74270 | 13.73 |
| 24.0486 | 3883.38 | 0.1003 | 3.69755 | 39.72 |
| 24.7644 | 3126.07 | 0.0802 | 3.59226 | 32.01 |
| 25.1081 | 657.73 | 0.0803 | 3.54386 | 6.74 |
| 25.7944 | 798.33 | 0.0802 | 3.45113 | 8.17 |
| 26.3269 | 299.82 | 0.1203 | 3.38352 | 3.07 |
| 27.2020 | 898.71 | 0.1003 | 3.27565 | 9.20 |
| 27.5899 | 1501.40 | 0.1203 | 3.23059 | 15.27 |
| 28.0772 | 447.16 | 0.1203 | 3.17650 | 4.58 |
| 28.3094 | 898.64 | 0.1203 | 3.14998 | 9.20 |
| 28.8654 | 1271.97 | 0.0802 | 3.08846 | 13.02 |
| 28.8690 | 1396.85 | 0.1003 | 3.08937 | 14.28 |
| 29.5713 | 1125.02 | 0.0802 | 3.01840 | 11.52 |
| 29.7519 | 509.47 | 0.0802 | 3.00046 | 5.22 |
| 30.3959 | 995.85 | 0.0802 | 2.91909 | 10.18 |
| 31.0963 | 2847.15 | 0.0802 | 2.87373 | 29.15 |
| 31.4449 | 885.65 | 0.1003 | 2.84249 | 9.07 |
| 31.6355 | 445.06 | 0.1203 | 2.82597 | 4.56 |
| 32.0966 | 391.71 | 0.1003 | 2.78642 | 4.01 |
| 32.5280 | 360.32 | 0.1203 | 2.75044 | 3.69 |
| 33.1135 | 237.31 | 0.2406 | 2.70313 | 2.43 |
| 34.0610 | 182.78 | 0.4813 | 2.62852 | 1.87 |
| 34.3860 | 373.19 | 0.1203 | 2.60590 | 3.81 |
| 34.7422 | 399.24 | 0.1604 | 2.58005 | 4.09 |
| 35.3962 | 330.22 | 0.0802 | 2.53387 | 3.38 |
| 36.2468 | 391.27 | 0.1203 | 2.47633 | 4.01 |
| 37.6973 | 340.66 | 0.1203 | 2.38432 | 3.49 |

Fig 2: DSC of compound of Formula-5
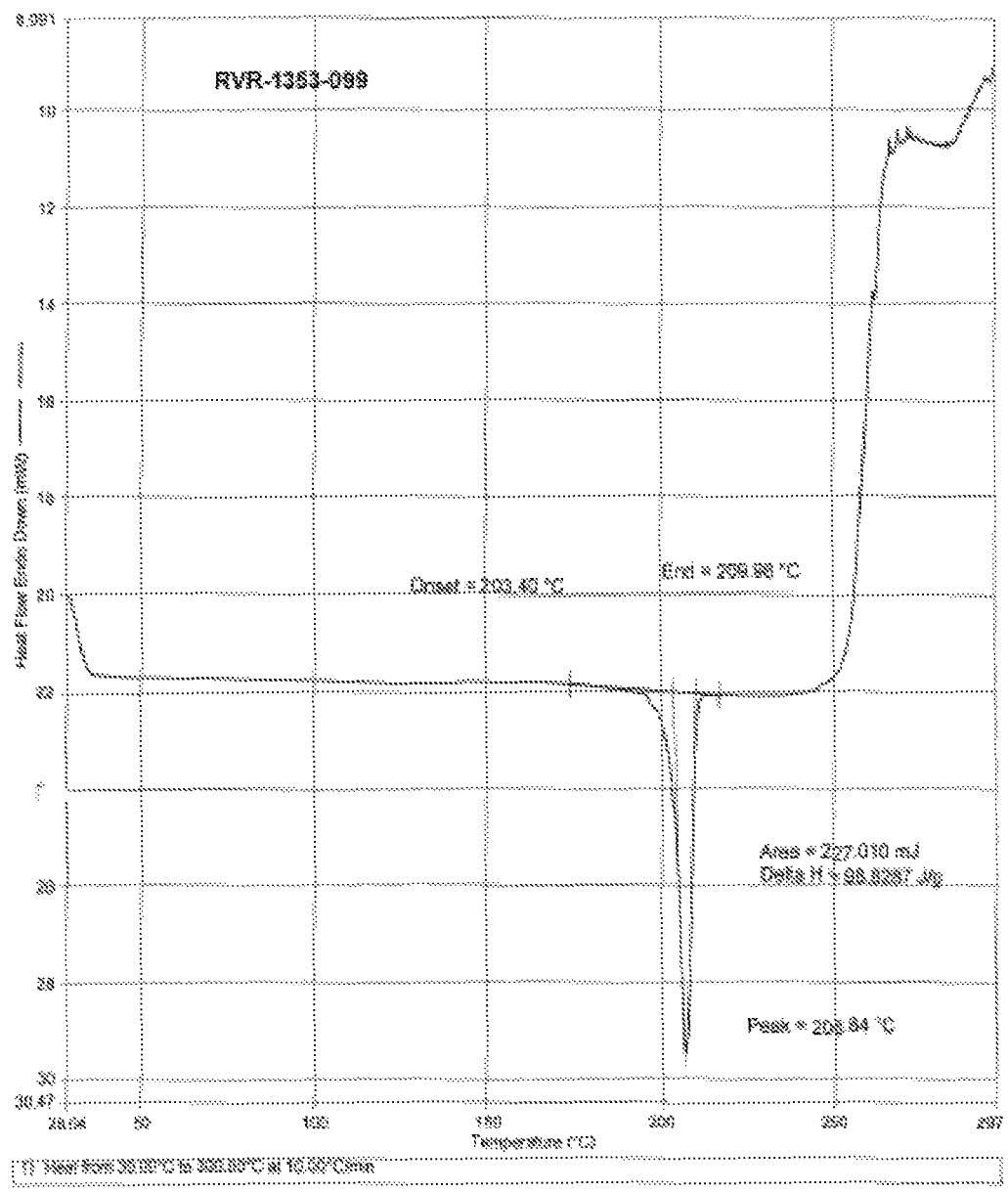

PROCESS FOR THE PREPARATION OF RIVAROXABAN INVOLVING NOVEL INTERMEDIATE

CROSS REFERENCE TO RELATED APPLICATIONS

The present application is a U.S. National Stage of International Application No. PCT/IB2017/058245 filed on Dec. 21, 2017, which claims priority to Indian Application No. 201721000351 filed on Jan. 4, 2017. Each of these applications is hereby incorporated by reference in its entirety for all purposes.

TECHNICAL FIELD

The present invention provides novel intermediate, process to prepare novel intermediate and an efficient and improved process for preparation of Rivaroxaban or its pharmaceutically acceptable salt using novel intermediate.

BACKGROUND OF THE INVENTION

Rivaroxaban chemically known as (S)-5-chloro-N-{[2-oxo-3-[4-(3-oxomorpholin-4-yl) phenyl]oxazolidin-5-yl]methyl} thiophene-2-carboxamide (FORMULA-1), is an oral anticoagulant and is marketed under brand name Xarelto. It is the first available orally active direct factor Xa inhibitor. On Jul. 1, 2011, the U.S. Food and Drug Administration (FDA) approved Rivaroxaban for prophylaxis of deep vein thrombosis (DVT), which may lead to pulmonary embolism (PE), in adults undergoing hip and knee replacement surgery. On Nov. 4, 2011, the U.S. FDA approved rivaroxaban for stroke prophylaxis in people with non-valvular atrial fibrillation.

FORMULA-1

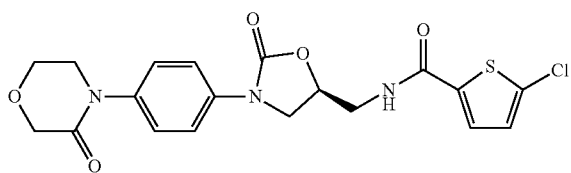

A process for the preparation of the Rivaroxaban and its intermediate was first disclosed in WO2001047919 (U.S. Pat. No. 7,157,456 B2) as shown in Scheme I, which includes: i. Reaction between I with aq. Methylamine in ethanol to produce 4-[{4-[(5 S)-5-(-Aminomethyl)-2-oxo-1,3-oxazolidin-3-yl]-phenyl}]-morpholin-3-one (Oxazolidine amine II);

Scheme I

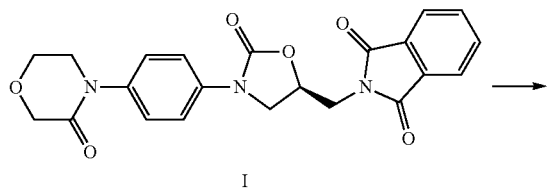

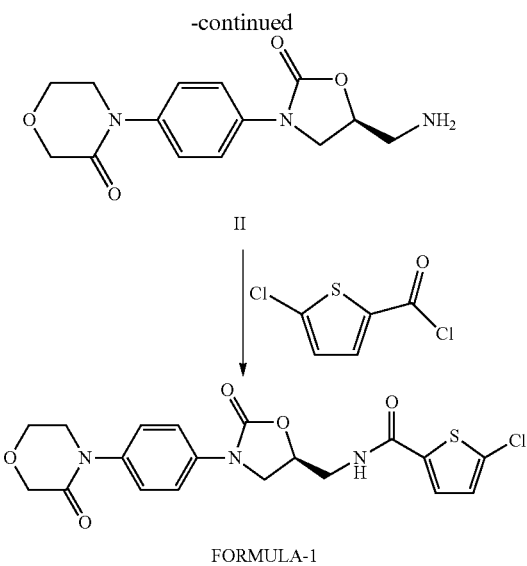

FORMULA-1 ii. Further condensation of 4-[{4-[(5 S)-5-(-Aminomethyl)-2-oxo-1,3-oxazolidin-3-yl]-phenyl}]-morpholin-3-one (Oxazolidine amine II) with 5-chlorothiophene-2-carbonyl chloride in pyridine to produce (S)-5-chloro-N{[2-oxo-3-[4-(3-oxomorpholin-4-yl)phenyl]oxazolidin-2-yl]methyl} thiophene-2-carboxamide (Rivaroxaban of FORMULA-1). In this process all intermediates and final API are purified using flash chromatography. Moreover use of excess dichloromethane and pyridine as a solvent limits its commercial scale production due to handling difficulties.

Similar process is disclosed in Journal of medicinal chemistry, 2005, 48, 5900-5908. U.S. Pat. No. 7,351,823 discloses a process to prepare rivaroxaban by slightly modifying the process disclosed in U.S. Pat. No. 7,157,456 to get the better yield of the product as compared to U.S. Pat. No. 7,157,456. However the yields of U.S. Pat. No. 7,157,456 still provide the scope for improvement. In the said process, intermediate VI in scheme I is converted into its hydrochloride salt and then reacted with 5-chlorothiophene-2-carbonyl chloride to get Rivaroxaban. The patent however does not mention the purity of the final product. Dimeric impurities are formed in the process disclosed in U.S. Pat. No. 7,351,823.

On the similar lines as that of U.S. Pat. No. 7,351,823, many processes for preparation of rivaroxaban have been claimed and disclosed in the patents thereafter, wherein the step of converting compound VI in scheme I to Rivaroxaban is modified.

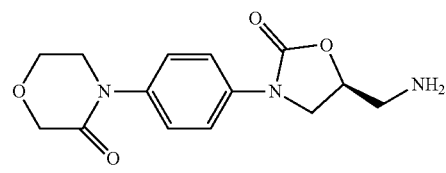

Compound VI the key intermediate

Either different salts of compound VI have been prepared or the base used in the reaction is changed or the solvents are selected in such a way that the yield, ease of handling and the affordability of the reaction of the overall process improves. U.S. Pat. No. 8,188,270 claims novel modifications and solvates of rivaroxaban and in Example 2. The patent discloses the process to prepare rivaroxaban in which compound VI as HCl salt is reacted with 5-chlorothiophene-2-carbonyl chloride in presence of triethyl amine and N-methyl-2-pyrrolidone (NMP) as solvent. Use of NMP in larger amount on industrial scale is undesirable, highly dangerous and environmentally unfriendly.

US2013253187 discloses a process to prepare rivaroxaban by reacting compound VI as its salt (preferably sulphate) with 5-chlorothiophene-2-carbonyl chloride in presence of organic base having pKa higher than 5.3, or mixtures thereof. Particularly preferred organic bases are organic bases with a pKa higher than 8.5, more preferably organic bases with a pKa higher than 10.0. The most preferred base being N,N-diisopropyl ethylamine (DIPEA). The application further mentions that, 'the use of an organic base instead of an inorganic base gives more versatility to the reaction' and 'the organic base easily dissolves in both organic media and water, which provides a more effective reaction and therefore better yield'. Use of excess of costly CDI, elaborate purification to separate byproducts from desired product and extensive purification process of two crystallizations to obtain pure Rivaroxaban compromises yields and makes the process lengthy and undesirable.

WO2013053739 provides a process to prepare rivaroxaban using compound VI, wherein compound VI is in its acid addition salt form and wherein the acid is specifically an organic acid. The drawback of the process are the extremely low yields (65-85%) of acid addition salts and conversion of acid addition salt to crude rivaroxaban gives product in not more than 90% yield. Further purification of this low yielded crude rivaroxaban decreases the yield of final pure rivaroxaban.

In WO2013120465 the process used in the preparation of acid addition salt of compound VI is:

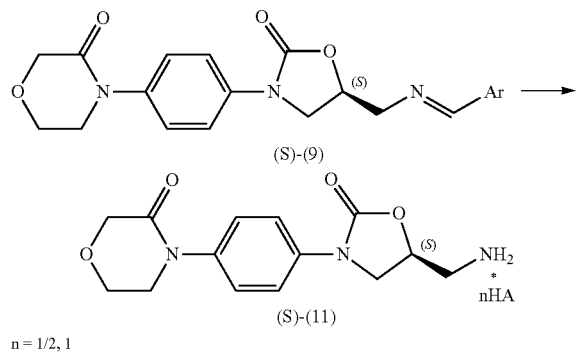

n = 1/2, 1 wherein HA stands for an acid selected from the group of methanesulfonic, benzenesulfonic, p-toluenesulfonic, (R)— and (S)— camphorsulfonic, hydrochloric, hydrobromic, phosphoric, nitric, sulphuric, D- and L-tartaric, benzoic, oxalic and trifluoroacetic acid. Use of unstable reagents such as aldehyde and imine, lower carbon efficiency, lengthy process to prepare Rivaroxaban via imine are undesirable features of the process. Also low yield of 51% in imine formation and 68% in coupling of imine with amino morpholine derivative, drastically reduces the overall yield of the process. Use costly & pyrophoric t-BuOLi makes process unsafe on larger scales and costly.

WO2013098833 provides compounds of formula VI in various inorganic and organic salt forms and their solid state forms. It claims a process to prepare rivaroxaban using these salts and rivaroxaban with high purity. The process uses sulphonyl halides to prepare rivaroxaban which are potential source of genotoxic impurity after reacting with alcoholic solvent. A process claimed by WO2015198259 uses Nitrate salt of compound VI and the overall yield of rivaroxaban is low.

It has been observed that plain base or an amine when treated with 5-chlorothiophene-2-carbonyl chloride leads to formation of Rivaroxaban with extremely poorer yields. It was also observed that when a salt of the amine is used for reaction with 5-chlorothiophene-2-carbonyl chloride, better yields and purity are obtained. It is also noticed that different salts give different purity and yield for the reaction. It makes it very clear that the amine is different from its salts in many aspects, primarily salts are significantly different from each other and from the amine from which they are formed. Different salts behave differently in the reaction. Stability and reactivity or the ability of different salts of amine to form quality of rivaroxaban is unpredictable. Therefore salts are not same as the amine from which they are formed.

In view of the drawbacks associated with prior art processes, there is a need to provide a better, highly energy efficient, cheap, safe process without the use of corrosive and pyrophoric chemicals, to prepare rivaroxaban which is suitable for industrial scale ups and which produces all the intermediates and the final product substantially free of impurities and in high yields.

OBJECT OF THE INVENTION

The main object of the present invention is to provide a process to prepare rivaroxaban using novel key intermediate, wherein the process is highly energy efficient, cheap, safe and easily scalable.

Another object of the invention is to provide novel key intermediates in the synthesis of rivaroxaban, which are high yielding, easily purified and easy to handle.

Yet another object of the invention is to provide a process to prepare key intermediate in the synthesis of rivaroxaban wherein the process is high yielding and easy to carry out on larger scale.

Yet another object of the invention is to provide highly pure crystalline form of the key intermediate in the synthesis of rivaroxaban.

Yet another object of the invention is provide a process to prepare a crystalline form of the key intermediate in the synthesis of rivaroxaban.

SUMMARY OF THE INVENTION

The present invention provides a process to prepare Rivaroxaban using 4-{4-[(5 S)-5-(Aminomethyl)-2-oxo-1,3-oxazolidin-3-yl]-phenyl}-morpholin-3-one perchlorate (Formula-5) as a novel key intermediate.

The present invention further provides a novel intermediate 4-{4-[(5 S)-5-(Aminomethyl)-2-oxo-1,3-oxazolidin-3-yl]-phenyl}-morpholin-3-one perchlorate (Formula-5).

The present invention provides a process to prepare 4-{4-[(5 S)-5-(Aminomethyl)-2-oxo-1,3-oxazolidin-3-yl]-phenyl}-morpholin-3-one perchlorate (Formula-5), wherein the process comprises:

i. reacting 2-{(5 S)-2-oxo-3-[(4-(3-oxo-4-morpholynyl) phenyl]-1,3-oxazolidine-5-yl}methyl-1H-isoindole-1,3 (2H)-dione of Formula-4 with methylamine to obtain amine of Formula-4a in-situ;

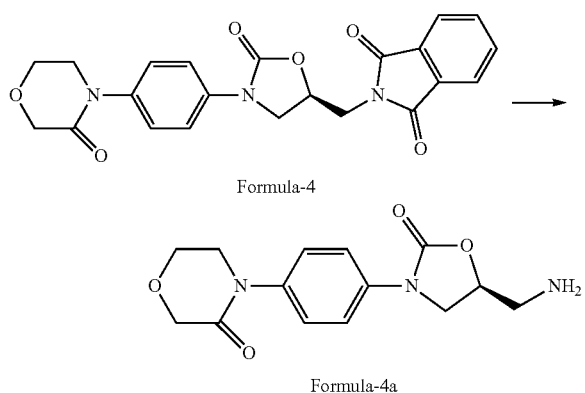

Formula-4

Formula-4a ii. converting in-situ prepared amine of Formula-4a in step i to 4-{4-[(5 S)-(Aminomethyl)-2-oxo-1,3-oxazolidin-3-yl]-phenyl}-morpholin-3-one perchlorate of Formula-5 by reacting it with Perchloric acid;

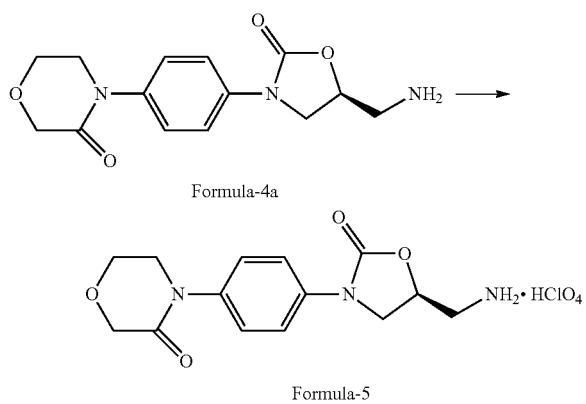

Formula-4a

Formula-5

In the present invention there is provided a crystalline 4-{4-[(5 S)-5-(Aminomethyl)-2-oxo-1,3-oxazolidin-3-yl]-phenyl}-morpholin-3-one perchlorate (Formula-5).

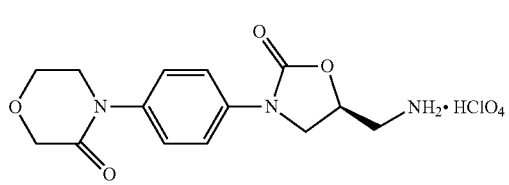

Formula-5

As per one more aspect of the present invention there is provided a process to prepare highly pure, crystalline form of 4-{4-[(5 S)-5-(Aminomethyl)-2-oxo-oxazolidin-3-yl]-phenyl}-morpholin-3-one perchlorate of Formula-5, wherein the process comprises the steps of:
  i. Crystallization of 4-{4-[(5 S)-5-(aminomethyl)-2-oxo-oxazolidin-3-]-phenyl}-morpholin-3-one perchlorate using solvent selected form methanol IPA, Ethanol, Dichloromethane or mixture thereof at a temperature of 30° C.-82° C.;
  ii. Separation of crystalline form of 4-{4-[(5 S)-5-(Aminomethyl)-2-oxo-oxazolidin-3-yl]-phenyl}-morpholin-3-one perchlorate from the solvent.

There is also provided a process to prepare rivaroxaban using crystalline form of 4-{4-[(5 S)-5-(Aminomethyl)-2-oxo-oxazolidin-3-yl]-phenyl}-morpholin-3-one perchlorate (Formula-5), wherein the process comprises:

BRIEF DESCRIPTION OF THE DRAWINGS

FIG. 1: XRPD pattern of crystalline form of 4-{4-[(5 S)-5-(Aminomethyl)-2-oxo-1,3-oxazolidin-3-yl]-phenyl}-morpholin-3-one perchlorate (Formula-5) Peak List: List of Peaks as depicted in FIG. 1

FIG. 2: Differential scanning calorimetry of 4-{4-[(5 S)-5-(Aminomethyl)-2-oxo-1,3-oxazolidin-3-yl]-phenyl}-morpholin-3-one perchlorate (Formula-5)

DETAILED DESCRIPTION OF THE INVENTION

The present invention provides a process to prepare Rivaroxaban using 4-{4-[(5 S)-5-(Aminomethyl)-2-oxo-oxazolidin-3-yl]-phenyl}-morpholin-3-one perchlorate of formula-5 as a novel key intermediate, wherein the process comprises:
  i. reacting 2-{(5 S)-2-oxo-3-[(4-(3-oxo-4-morpholynyl)phenyl]-1,3-oxazolidine-5-yl}methyl-1H-isoindole-1,3 (2H)-dione of Formula-4 with aqueous methylamine to obtain amine of Formula-4a in-situ;

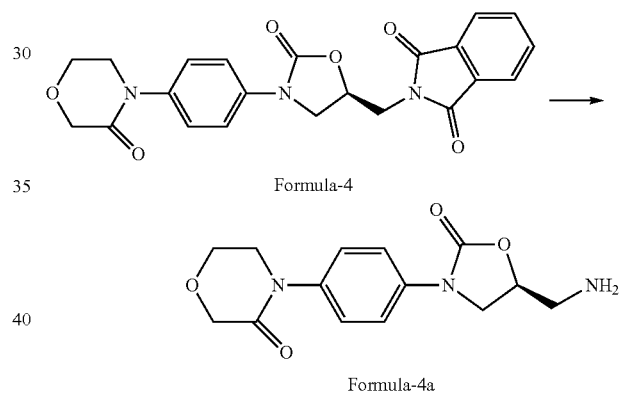

Formula-4

Formula-4a ii. converting in-situ prepared amine of Formula 4a in step i to 4-{4-[(5 S)-(Aminomethyl)-2-oxo-1,3-oxazolidin-3-yl]-phenyl}-morpholin-3-one perchlorate of Formula-5 by reacting it with Perchloric acid;

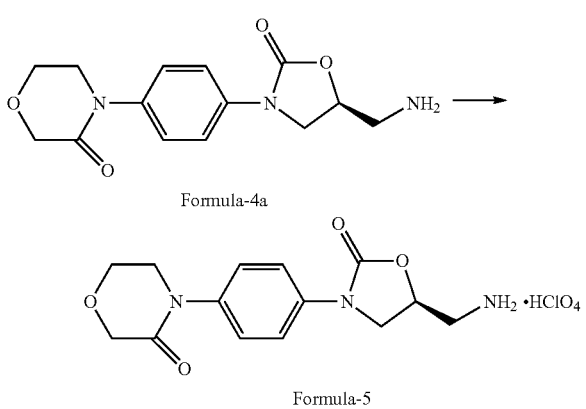

Formula-4a

Formula-5 iii. reacting 4-{4-[(5 S)-(Aminomethyl)-2-oxo-1,3-oxazolidin-3-yl]-phenyl}-morpholin-3-one perchlorate of Formula-5, obtained in step ii with 5-chlorothiophene-2-carbonyl chloride in presence of a base and solvent to obtain Rivaroxaban of Formula-1.

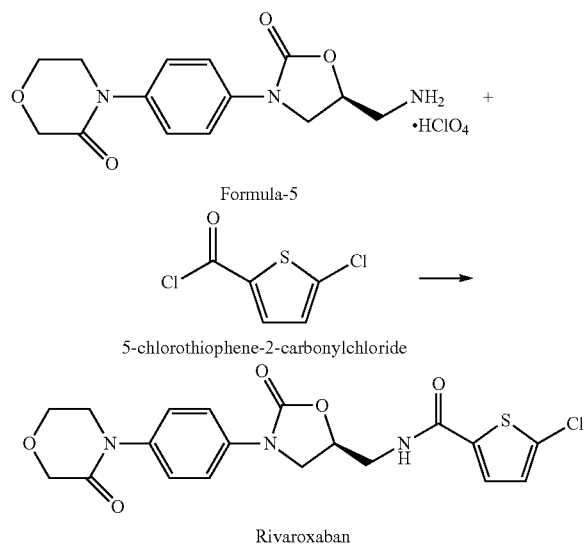

Formula-5

5-chlorothiophene-2-carbonylchloride

Rivaroxaban

The compound of the Formula-4 is prepared by the processes known in the prior art. The reaction in step i is carried out using excess of aqueous methylamine in presence of solvent selected from methanol, ethanol, isopropyl alcohol (IPA), water or mixture thereof; preferably IPA, at temperature from 30° C. to 60° C. preferably at 45° C. to 50° C. The in-situ prepared amine in step i is acidified using perchloric acid in the same solvent as that in step i to produce 4-{4-[(5 S)-(Aminomethyl)-2-oxo-1,3-oxazolidin-3-yl]-phenyl}-morpholin-3-one perchlorate of Formula-5.

4-{4-[(5 S)-(Aminomethyl)-2-oxo-1,3-oxazolidin-3-yl]-phenyl}-morpholin-3-one perchlorate of Formula-5 formed in step ii is in crystalline form. Formula-5 in its crystalline form is used as a starting material in the synthesis of rivaroxaban in step iii.

The reaction between perchlorate of Formula-5 with 5-chlorothiophene-2-carbonyl chloride as in step iii is carried out in presence of an inorganic base selected from Sodium bicarbonate, Sodium carbonate, Potassium bicarbonate, Potassium carbonate, Lithium carbonate, or an organic base selected from Triethylamine, N,N diisopropylethyl amine, Pyridine; preferably Sodium carbonate in a solvent selected from ketones such as Acetone, Methyl ethyl ketone, N-methylpyroolidone, Methyl isobutyl ketone (MIBK), aromatic hydrocarbons such as Toluene, Xylene, chlorinated solvents such as Dichloromethane, Chloroform, Chlorobenzene, esters such as Ethyl acetate, Methyl acetate, amides such as Dimethylformamide, Dimethylacetamide, or solvents selected from Acetonitrile, water, Dimethyl sulfoxide, ethers such as Tetrahydrofuran, Dioxane, and mixtures thereof, preferably in mixture of Acetone, Toluene and water, in the ratio of 2.4:2.2:5.17.

Final yield of Rivaroxaban was upto 98%. The purity of final product was as per ICH standards. The process of the present invention was high yielding as compared to processes in the prior art. Raw materials used in the process were cheap and easy to handle, thus making the process cost effective, energy efficient and highly efficient.

Use of perchloric acid to form 4-{4-[(5 S)-5-(Aminomethyl)-2-oxo-1,3-oxazolidin-3-yl]-phenyl}-morpholin-3-one perchlorate is normally unheard of. The reason may be that the perchloric acid per se is highly reactive and has strong oxidizing effect. The reason may be the fact that perchloric acid being a very strong oxidizing agent and oxidizes the compound very fast, the moment it comes into contact with it. As a result an effort to form a salt with perchloric acid may result into unstable salt and would foul the purpose of preparing a perchloric acid salt.

However, surprisingly it was noticed that 4-{4-[(5 S)-5-(Aminomethyl)-2-oxo-1,3-oxazolidin-3-yl]-phenyl}-morpholin-3-one perchlorate is stable, highly pure, crystalline and is produced in very good yields.

Unlike the salts used in the prior art, perchlorate salt was found to be high yielding making the process efficient, easy to handle therefore easily scalable and could be prepared in situ in reaction mixture during amine preparation. It also gives highly pure product, both the salt as well as rivaroxaban in the next step. Use of 4-{4-[(5 S)-5-(Aminomethyl)-2-oxo-1,3-oxazolidin-3-yl]-phenyl}-morpholin-3-one perchlorate (Formula-5) of Formula-5 as a key intermediate in the synthesis of rivaroxaban makes the entire process cost effective, energy efficient and easily scalable.

US2013253187 states that the use of organic base in the reaction between sulphate of 4-{4-[(5 S)-(Aminomethyl)-2-oxo-1,3-oxazolidin-3-yl]-phenyl}-morpholin-3-one and 5-chlorothiophene-2-carbonyl chloride, provides a more effective reaction and therefore better yield. Surprisingly it was noticed that, Sodium carbonate, an inorganic base, made this reaction high yielding, easy to handle and highly efficient. Also the cost of inorganic base as compared to DIPEA, used in US 2013253187 is considerably less, making process cheaper. The yields of reaction in present invention are better than those of US 2013253187. Also the time required in the present invention to prepare rivaroxaban is lesser than that disclosed in US2013253187. Use of inorganic bases makes the process user friendly and nature friendly. As per one aspect of the invention, there is provided 4-[4-[(5 S)-5-(Aminomethyl)-2-oxo-1,3-oxazolidin-3-yl]-phenyl}-morpholin-3-one perchlorate (Formula-5).

Formula-5

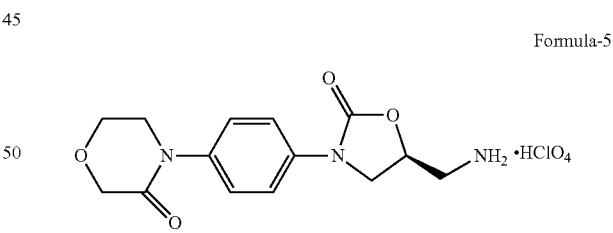

It was surprisingly found that as compared to other known salts of 4-{4-[(5 S)-5-(Aminomethyl)-2-oxo-1,3-oxazolidin-3-yl]-phenyl}-morpholin-3-one, the yield of 4-{4-[(5 S)-5-(Aminomethyl)-2-oxo-1,3-oxazolidin-3-yl]-phenyl}-morpholin-3-one perchlorate (Formula-5) was high and the product obtained was in highly pure form. Surprisingly it was noticed that although perchloric acid is a strong oxidizing agent, use of perchloric acid could yield a stable salt. The salt was easy to handle and easily scalable. The yield of 4-{4-[(5 S)-5-(Aminomethyl)-2-oxo-1,3-oxazolidin-3-yl]-phenyl}-morpholin-3-one perchlorate was higher than that of widely used hydrochloric acid salt mentioned in prior art U.S. Pat. No. 7,351,823.

In another aspect of the invention, there is provided a process to prepare 4-{4-[(5 S)-5-(Aminomethyl)-2-oxo-1,3-oxazolidin-3-yl]-phenyl}-morpholin-3-one perchlorate (Formula-5), wherein the process comprises;

i. reacting 2-{(5 S)-2-oxo-3-[(4-(3-oxo-4-morpholynyl)phenyl]-1,3-oxazolidine-5-yl}methyl-1H-isoindole-1,3 (2H)-dione of Formula-4 with methylamine to obtain amine of Formula-4a in-situ;

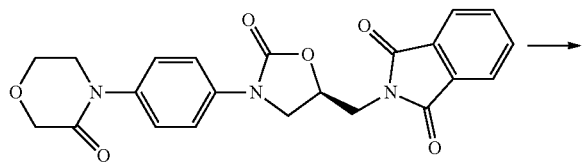

Formula-4

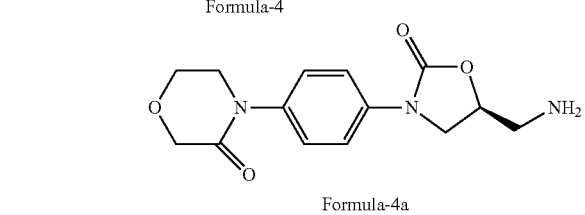

Formula-4a ii. converting in-situ prepared amine of Formula-4a in step i to 4-{4-[(5 S)-(Aminomethyl)-2-oxo-1,3-oxazolidin-3-yl]-phenyl}-morpholin-3-one perchlorate of Formula-5 by reacting it with Perchloric acid;

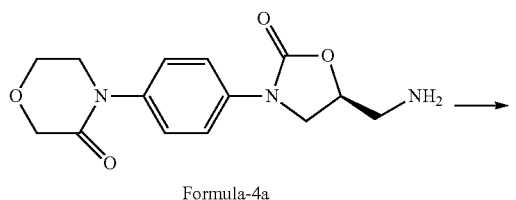

Formula-4a

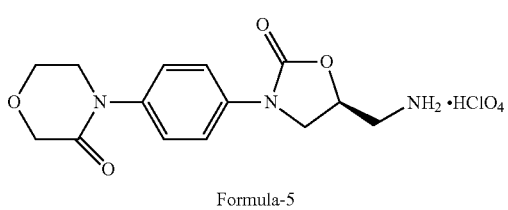

Formula-5

The reaction in step i is carried out using excess of aqueous methylamine in presence of solvent selected from methanol, ethanol, IPA water or mixture thereof; preferably IPA, at temperature from 30° C. to 60° C. preferably at 45° C. to 50° C. The in-situ obtained amine is acidified using perchloric acid to produce 4-{4-[(5 S)-(Aminomethyl)-2-oxo-1,3-oxazolidin-3-yl]-phenyl}-morpholin-3-one perchlorate of Formula-5.

In another aspect of the invention there is provided a highly pure crystalline form of 4-{4-[(5 S)-5-(Aminomethyl)-2-oxo-1,3-oxazolidin-3-yl]-phenyl}-morpholin-3-one perchlorate (Formula-5).

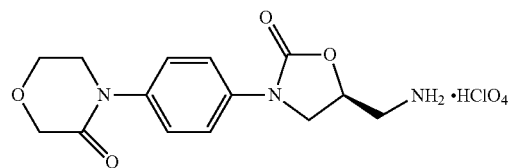

Formula-5

Crystalline form of 4-{4-[(5 S)-5-(Aminomethyl)-2-oxo-1,3-oxazolidin-3-yl]-phenyl}-morpholin-3-one perchlorate (Formula-5) is characterized by XRPD pattern with 2θ values at 10.26, 19.27, 20.24, 20.58, 24.04 and 31.09+/−0.2θ.

Crystalline form of 4-{4-[(5 S)-5-(Aminomethyl)-2-oxo-1,3-oxazolidin-3-yl]-phenyl}-morpholin-3-one perchlorate (Formula-5) is characterized by XRPD pattern with 2θ values at 10.26, 13.70, 19.67, 20.37, 23.08, 24.76+/−0.2θ.

Crystalline form of 4-{4-[(5 S)-5-(Aminomethyl)-2-oxo-1,3-oxazolidin-3-yl]-phenyl}morpholin-3-one perchlorate (Formula-5) is characterized by XRPD pattern with 2θ values at 13.70, 19.27, 20.24, 20.37, 24.04+/−0.2θ.

Accordingly, crystalline form of 4-{4-[(5 S)-5-(Aminomethyl)-2-oxo-1,3-oxazolidin-3-yl]-phenyl}-morpholin-3-one perchlorate (Formula-5) is characterized by XRPD pattern with 2θ values at 10.26, 13.70, 19.27, 19.67, 20.24, 20.37, 20.58, 23.08, 24.04, 24.76 and 31.09+/−0.2θ.

The crystalline form of 4-{4-[(5 S)-5-(Aminomethyl)-2-oxo-1,3-oxazolidin-3-yl]-phenyl}-morpholin-3-one perchlorate (Formula-5) is further characterized by the XRPD pattern with 2θ values at 12.81, 13.17, 14.31, 14.58, 16.84, 18.94, 21.25, 21.39, 21.88, 22.33, 23.75, 27.58, 28.88, 29.06, 29.57, 30.59, +/−0.2θ.

The crystalline form of 4-{4-[(5 S)-5-(Aminomethyl)-2-oxo-1,3-oxazolidin-3-yl]-phenyl}-morpholin-3-one perchlorate (Formula-5) is characterized by the XRPD pattern as shown in FIG. 1.

The crystalline form is further characterized by DSC. The product showed DSC endotherm at 206.84° C. as shown in FIG. 2.

A compound is said to be in highly pure form, when the purity of the compound is measured by HPLC and gives value of more than 99%.

As per one aspect of the invention there is provided a process to prepare highly pure crystalline form of 4-{4-[(5 S)-5-(Aminomethyl)-2-oxo-1,3-oxazolidin-3-yl]-phenyl}-morpholin-3-one perchlorate (Formula-5), wherein the process comprises the steps of:

i. reacting 2-{(5 S)-2-oxo-3-[(4-(3-oxo-4-morpholynyl)phenyl}-1,3-oxazolidine-5-yl]methyl-1H-isoindole-1,3 (2H)-dione of Formula-4 with methylamine to obtain amine of Formula-4a in-situ;

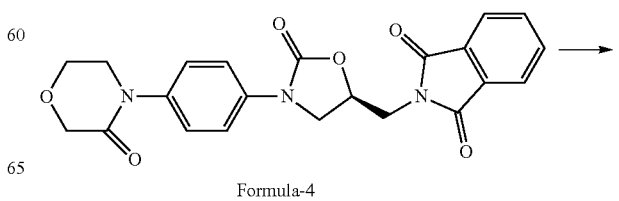

Formula-4

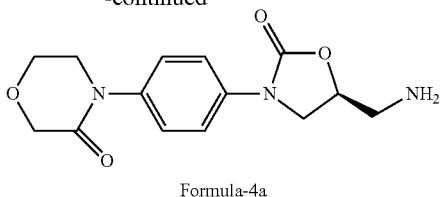

Formula-4a ii. converting in-situ prepared amine of Formula-4a in step i to 4-{4-[(5 S)-(Aminomethyl)-2-oxo-1,3-oxazolidin-3-yl]-phenyl}-morpholin-3-one perchlorate of Formula-5 by reacting it with Perchloric acid;

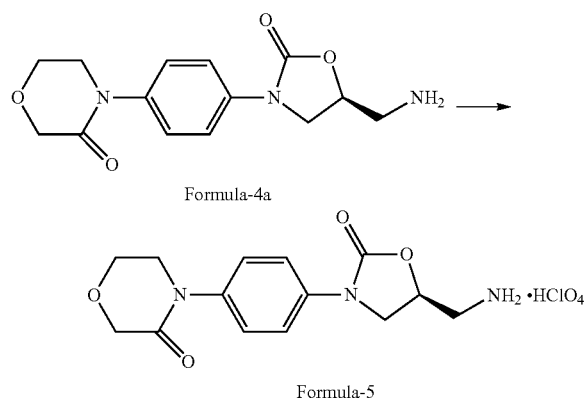

iii. crystallizing 4-{4-[(5 S)-5-(Aminomethyl)-2-oxo-1,3-oxazolidin-3-yl]-phenyl}-morpholin-3-one perchlorate of Formula-5 obtained in step ii in a solvent selected from Acetic acid, methanol, IPA, ethanol, Dichloromethane and mixture thereof at a temperature of 30° C. to 82° C. to obtain crystals of 4-{4-[(5 S)-(Aminomethyl)-2-oxo-1,3-oxazolidin-3-yl]-phenyl}-morpholin-3-one perchlorate of Formula 5.

iv. Separating crystal of 4-{4-[(5 S)-5-(Aminomethyl)-2-oxo-1,3-oxazolidin-3-yl]-phenyl}-morpholin-3-one perchlorate from the solvent.

The reaction in step i is carried out using excess of aqueous methylamine in presence of solvent selected from methanol, ethanol, IPA water or mixture thereof; preferably IPA, at temperature from 30° C. to 60° C. preferably at 45° C. to 50° C. The amine obtained in step i is acidified using perchloric acid to produce 4-{4-[(5 S)-5-(Aminomethyl)-2-oxo-1,3-oxazolidin-3-yl]-phenyl}-morpholin-3-one perchlorate of Formula-5.

Crystallization of 4-{4-[(5 S)-(Aminomethyl)-2-oxo-1,3-oxazolidin-3-yl]-phenyl}-morpholin-3-one perchlorate is carried out using solvent selected from acetic acid, methanol, IPA, ethanol, dichloromethane or mixture thereof; preferably in the mixture of dichloromethane and methanol in the ratio of 1:3 to 3:1, preferred being 4:2, at a temperature of 30° C. to 82° C. The crystals of Formula-5 were separated by Filtration.

As described earlier, the very nature of perchloric acid discourages its use to form a salt for use in the reactions. Surprisingly the crystal form of Formula 5 was found to be stable, and was produced in very good yields with excellent purity. The deprotection reaction was carried out in Isopropyl alcohol. When the perchloric acid was added to the reaction mass 4-{4-[(5 S)-5-(Aminomethyl)-2-oxo-1,3-oxazolidin-3-yl]-phenyl}-morpholin-3-one perchlorate of Formula 5 separated out from the reaction mass.

Surprisingly, the accidentally obtained crystalline 4-{4-[(5 S)-5-(Aminomethyl)-2-oxo-1,3-oxazolidin-3-yl]-phenyl}-morpholin-3-one perchlorate of Formula 5 is obtained in high yield (94%) and in highly pure form. This negated the necessity to purify intermediates separately and therefore made the process cost effective, easy to perform, industrially scalable and environment friendly. This also gave the pure rivaroxaban in high yield and purity.

The very fact that use of perchlorate i.e. 4-{4-[(5 S)-5-(Aminomethyl)-2-oxo-1,3-oxazolidin-3-yl]-phenyl}-morpholin-3-one perchlorate results into better yields and better purity of Rivaroxaban than use of mere 4-{4-[(5 S)-5-(Aminomethyl)-2-oxo-1,3-oxazolidin-3-yl]-phenyl}-morpholin-3-one means the two are not same and cannot be presumed to be same.

These two are technically, structurally and constitutionally dissimilar and are not superimposable. They significantly differ in their performance in reaction dynamics because of inherent differences in them which result into differential yields and purity of the product.

The below given examples demonstrate best mode of carrying out the present invention and do not limit invention in any manner.

EXAMPLES

Example-1

Preparation of 2-(2 R)-hydroxy-3-{[4-(3-oxo-4-morphonyl)phenylamino]propyl}-1H-isoindole-1,3 (2H)-dione (Formula-3) from 4-(4-aminophenyl) morpholinone (Formula-2) and (S)-(+)glycidyl phthalimide

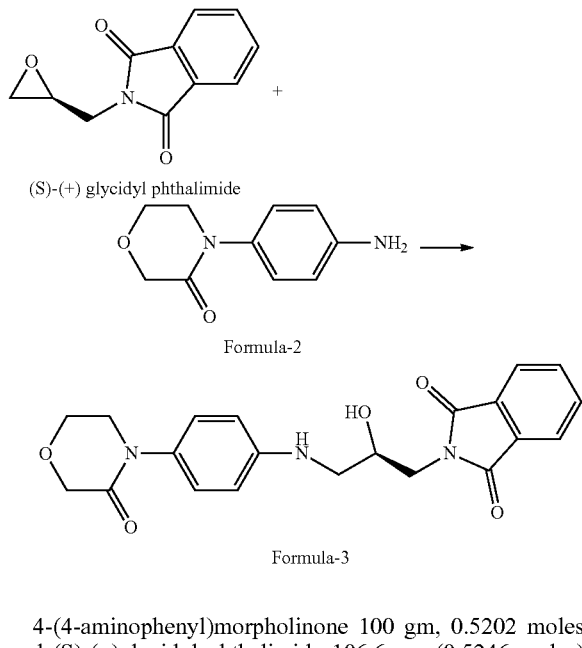

4-(4-aminophenyl)morpholinone 100 gm, 0.5202 moles and (S)-(+)glycidyl phthalimide 106.6 gm (0.5246 moles) was charged to the mixture of, methanol and water 1000 ml (9:1) and heated to 65° C.-70° C. Continued stirring for next 20 hrs at 65° C.-70° C. Add second lot of S)-(+)glycidyl phthalimide 10.6 gm (0.05246 moles) and 200 ml (9:1)

methanol water mixture and stir for next 12 hrs. Cooled the reaction mass to 25° C.-30° C. and filter the slurry on Buckner funnel, suck dried well. Wet cake washed with 100 ml mixture of methanol and water (9:1). The solid obtained was dried at 50° C. to 55° C. to get 190 gm compound of Formula-3 as dry material. Yield-92%

Example-2

Preparation of 2-{(5 S)-2-oxo-3-[4-(3-oxo-4-morpholynyl)phenyl]-1,3-oxazolidine-5-yl}methyl-1H-isoindole-1,3 (2H)-dione (Formula-4) from 2-(2 R)-hydroxy-3-{[4-(3-oxo-4-morphonyl)phenylamino]propyl}-1H-isoindole-1,3(2H)-dione (Formula-3)

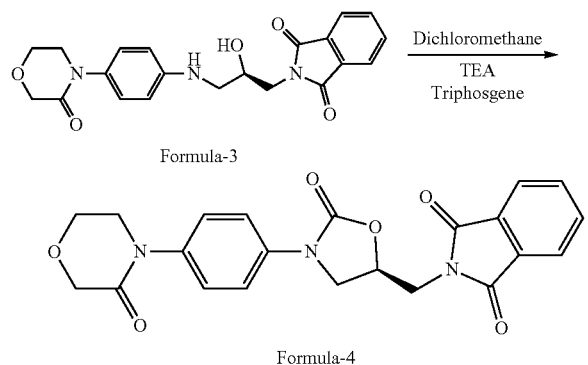

Amino alcohol 170 gm, 0.4293 moles and Triethylamine 4114.72 gms, 0.9459 moles, was charged to Dichloromethane 2380 ml and cooled reaction mass to 0° C.-5° C. To the cooled reaction mass added triphosgene solution, 51.09 gms in 340 ml MDC, 0.18 moles drop wise at 5° C.-10° C. in 60 min, and stirred for 60-90 min. Reaction mass quenched with water and distilled out MDC layer atmospherically till thick solid mass obtained. To the thick solid, charged tetrahydrofuran 1360 ml, distilled out 130 ml under vacuum. Cooled slurred mass to 25° C.-30° C., stirred for 30 min, filtered. Wet material dried at 55° C.-60° C. to afford 162 gm dry material. Yield-89%

Example-3

Preparation of 4-{4-[(5S)-(Aminomethyl)-2-oxo-1,3-oxazolidin-3-yl]-phenyl}-morpholin-3-one perchlorate (Formula-5) and its crystalline form from 2-{(5 S)-2-oxo-3-[4-(3-oxo-4-morpholynyl)phenyl]-1,3-oxazolidine-5-yl}methyl-1H-isoindole-1,3 (2H)-dione (Formula-4)

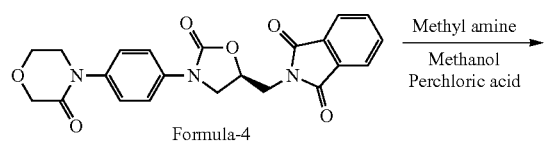

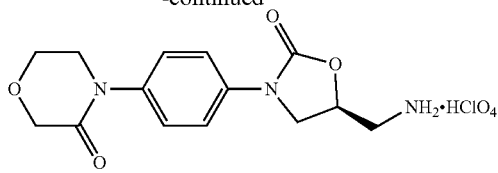

To the slurry of Formula-4 160 gm, 0.379 moles in 800 ml Isopropyl alcohol, Charged 40% methylamine solution 130 gm, 1.677 moles. Reaction mass was heated up to 45° C.-50° C. for 2-3 Hrs. Distilled out IPA under vacuum and charged fresh 800 ml Isopropyl alcohol Cooled reaction mass to 45° C.-50° C. and added 70% solution of Perchloric acid 59.6 gm, 0.415 moles. Stirred reaction mass for 1 Hrs at 45-50° C. Cooled reaction mass to 0-5° C., filtered and dried at 50° C.-55° C. to afford 160 gm crude 4-{4-[(5 S)-5-(Aminomethyl)-2-oxo-1,3-oxazolidin-3-yl]-phenyl}-morpholin-3-one perchlorate. The crude 4-{4-[(5 S)-5-(Aminomethyl)-2-oxo-1,3-oxazolidin-3-yl]-phenyl}-morpholin-3-one perchlorate has a crystalline nature and is in considerably pure form.

Preparation of pure crystalline 4-{4-[(5 S)-(Aminomethyl)-2-oxo-1,3-oxazolidin-3-yl]-phenyl}-morpholin-3-one perchlorate (Formula-5) from crude To Above crude 4-{4-[(5 S)-5-(Aminomethyl)-2-oxo-1,3-oxazolidin-3-yl]-phenyl}-morpholin-3-one perchlorate charged 640 ml Dichloromethane (4 vol of starting material) and charged 320 ml methanol. Heated the slurry to 38° C.-40° C. and stirred for 30 min. Cooled the slurry to 20° C. Filtered and suck dried. Product obtained after drying was 138.7 gm pure crystalline perchlorate salt having purity more than 99.5% (Yield-94%)

Example-4

Preparation of Rivaroxaban from 4-{4-[(5S)-(Aminomethyl)-2-oxo-1,3-oxazolidin-3-yl]-phenyl}-morpholin-3-one perchlorate (Formula-5)

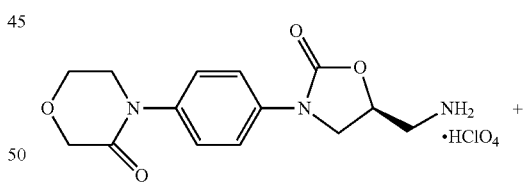

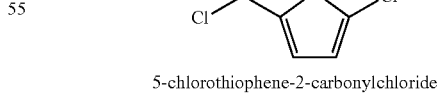

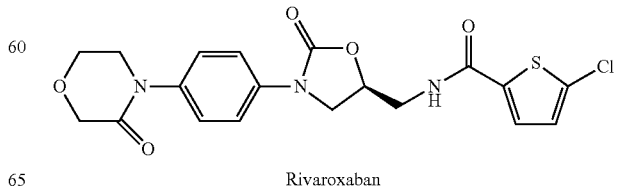

To the chilled solution of sodium carbonate 5.83 gm, 0.55 moles in 51 ml water, charged 10 gms, (0.0255 moles) of compound of Formula-5 followed by acetone 24 ml. Stirred for 10 min., Meanwhile prepared dil. solution of 5-chlorothiophene-2-carbonyl chloride (5.7 gm Chloro compound diluted with 22 ml of toluene). Toluene solution of 5-chlorothiophene-2-carbonyl chloride was added drop wise at 0° C.-5° C., to the reaction mass. White solid separated out during addition of Toluene solution. Stirred for next 30 min at 0° C.-5° C., raised the temperature of reaction mass to 50° C. and charged 35 ml acetone. Stirred for 30 min at 45° C. to 50° C., followed by cooling and filtration, wet cake was slurred in water at 55° C.-60° C. to afford 10.9 gms dry product (Yield-98%).

Above material was purified using methanol Dichloromethane mixture followed by acetic acid to afford pure material having HPLC purity 99.8% chiral purity-99.95%.

We claim:

1. A process to prepare rivaroxaban using 4-{4-[(5S)-(Aminomethyl)-2-oxo-1,3-oxazolidin-3-yl]-phenyl}-morpholin-3-one perchlorate (Formula-5), wherein the process comprises:
   i. reacting 2-{(5S)-2-oxo-3-[(4-(3-oxo-4-morpholynyl)phenyl]-1,3-oxazolidine-5-yl}methyl-1H-isoindole-1,3(2H)-dione of Formula-4 with aqueous methylamine to obtain amine of Formula-4a in-situ:

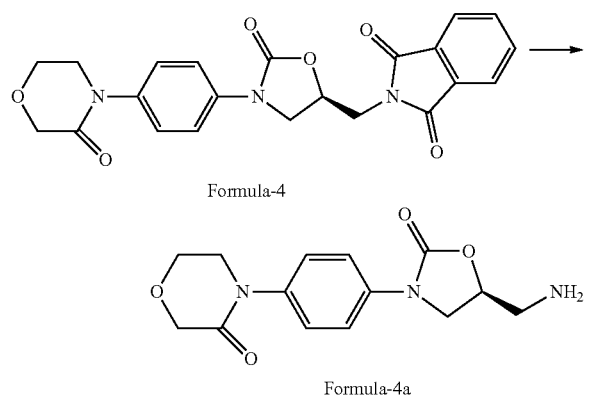

Formula-4

Formula-4a ii. converting in-situ prepared amine of Formula 4a in step i to 4-{4-[(5S)-(Aminomethyl)-2-oxo-1,3-oxazolidin-3-yl]-phenyl}-morpholin-3-one perchlorate of Formula-5 by reacting it with Perchloric acid;

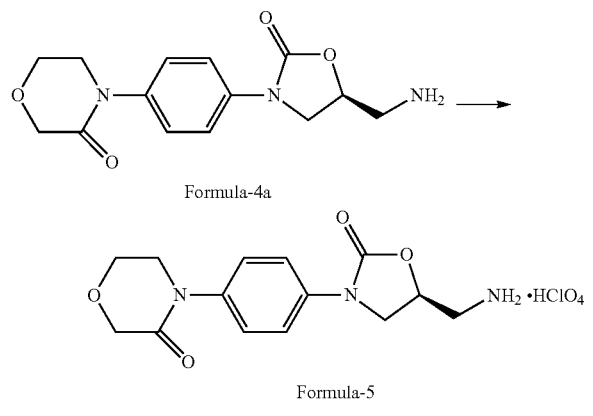

Formula-4a

Formula-5 iii. reacting 4-{4-[(5S)-(Aminomethyl)-2-oxo-1,3-oxazolidin-3-yl]-phenyl}-morpholin-3-one perchlorate of Formula-5, obtained in step ii with 5-chlorothiophene-2-carbonyl chloride in presence of a base and solvent to obtain Rivaroxaban of Formula-1.

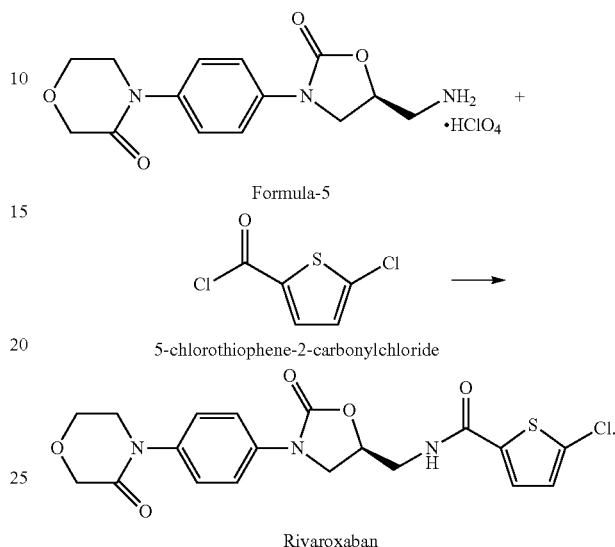

Formula-5

5-chlorothiophene-2-carbonylchloride

Rivaroxaban

2. The process as claimed in claim 1, wherein a solvent in step i and ii is selected from methanol, ethanol, isopropyl alcohol, or water or mixture thereof.

3. The process as claimed in claim 1, wherein the base used in step iii is selected from an inorganic base selected from sodium bicarbonate, sodium carbonate, potassium bicarbonate, potassium carbonate, or lithium carbonate, or an organic base selected from triethylamine, N,N-diisopropylethyl amine, or pyridine.

4. The process as claimed in claim 1, wherein the solvent used in step iii is selected from the group consisting of:
   a. ketones selected from acetone, methyl ethyl ketone, N-methylpyroolidone, or MIBK;
   b. aromatic hydrocarbons selected from toluene or xylene;
   c. chlorinated solvents selected from dichloromethane, chloroform or chlorobenzene;
   d. esters selected from ethyl acetate, or methyl acetate;
   e. amides selected from dimethylformamide or dimethylacetamide;
   f. solvents selected from acetonitrile, water, dimethyl sulfoxide; and
   g. ethers selected from tetrahydrofuran, or dioxane; and
   h. mixtures thereof.

5. The process as claimed in claim 4, wherein the mixture of acetone, toluene and water is in the ratio of 2.4:2.2:5.17.

6. The process as claimed in claim 1, wherein 4-{4-[(5S)-(Aminomethyl)-2-oxo-1,3-oxazolidin-3-yl]-phenyl}-morpholin-3-one perchlorate (Formula-5) formed in step ii is in crystalline form.

7. The process as claimed in claim 6, wherein the crystalline form of 4-{4-[(5S)-(Aminomethyl)-2-oxo-1,3-oxazolidin-3-yl]-phenyl}-morpholin-3-one perchlorate (Formula-5) is characterized by XRPD pattern with 2θ values at 10.26, 13.70, 19.67, 20.37, 23.08, 24.76+/−0.2θ.

8. The process as claimed in claim 6, wherein the crystalline form of 4-{4-[(5S)-(Aminomethyl)-2-oxo-1,3-oxazolidin-3-yl]-phenyl}-morpholin-3-one perchlorate (Formula-5) is prepared by the process comprises the steps of:

1. crystallizing 4-{4-[(5S)-(Aminomethyl)-2-oxo-1,3-oxazolidin-3-yl]-phenyl}-morpholin-3-one perchlorate in a crystallizing solvent at a temperature of 30° C. to 82° C.; and
2. separating crystals of 4-{4-[(5S)-(Aminomethyl)-2-oxo-1,3-oxazolidin-3-yl]-phenyl}-morpholin-3-one perchlorate from the crystallizing solvent.

9. The process as claimed in claim 8, wherein in step i the crystallizing solvent is selected from acetic acid, methanol, isopropyl alcohol, ethanol, or dichloromethane or mixture thereof.

10. The process as claimed in claim 1, wherein the process comprises 4-{4-[(5S)-(Aminomethyl)-2-oxo-1,3-oxazolidin-3-yl]-phenyl}-morpholin-3-one perchlorate (Formula-5) as a key intermediate.

11. The process as claimed in claim 10, wherein 4-{4-[(5S)-(Aminomethyl)-2-oxo-1,3-oxazolidin-3-yl]-phenyl}-morpholin-3-one perchlorate (Formula-5) is prepared by the process comprising;
   1. reacting 2-{(5S)-2-oxo-3-[(4-(3-oxo-4-morpholynyl)phenyl]-1,3-oxazolidine-5-yl}methyl-1H-isoindole-1,3 (2H)-dione of Formula-4 with methylamine to obtain amine of Formula-4a in-situ;

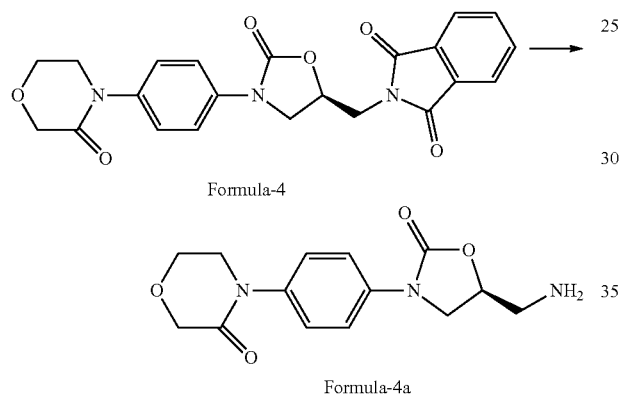

Formula-4

Formula-4a 2. converting in-situ prepared amine of Formula-4a in step i to 4-{4-[(5S)-(Aminomethyl)-2-oxo-1,3-oxazolidin-3-yl]-phenyl}-morpholin-3-one perchlorate of Formula-5 by reacting it with perchloric acid;

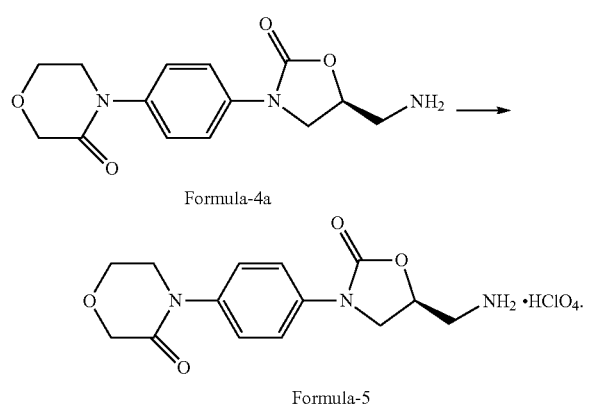

Formula-4a

Formula-5

12. The process as claimed in claim 9, wherein in step i), the crystallizing solvent is a mixture of dichloromethane and methanol in the ratio of 1:3 to 3:1.

13. A process to prepare 4-{4-[(5S)-(Aminomethyl)-2-oxo-1,3-oxazolidin-3-yl]-phenyl}-morpholin-3-one perchlorate (Formula-5) wherein the process comprises;
   i. reacting 2-{(5S)-2-oxo-3-[(4-(3-oxo-4-morpholynyl)phenyl]-1,3-oxazolidine-5-yl}methyl-1H-isoindole-1,3 (2H)-dione of Formula-4 with methylamine to obtain amine of Formula-4a in-situ;

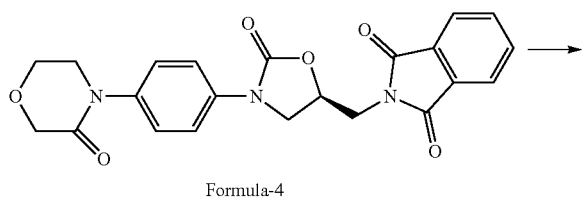

Formula-4

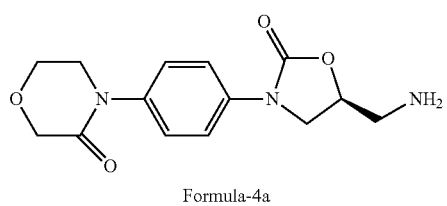

Formula-4a ii. converting in-situ prepared amine of Formula-4a in step i to 4-{4-[(5S)-(Aminomethyl)-2-oxo-1,3-oxazolidin-3-yl]-phenyl}-morpholin-3-one perchlorate of Formula-5 by reacting it with Perchloric acid;

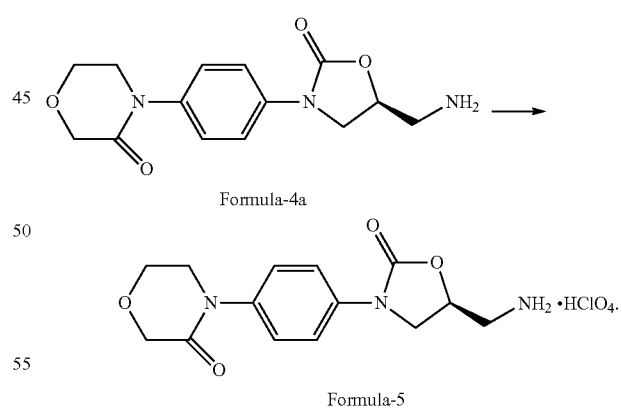

Formula-4a

Formula-5

14. The process as claimed in claim 13, wherein a solvent in step i and ii is selected from methanol, ethanol, IPA water or mixture thereof.

* * * * *